United States Patent
Beatty et al.

(10) Patent No.: US 11,661,624 B2
(45) Date of Patent: May 30, 2023

(54) METHODS OF IDENTIFYING AND CHARACTERIZING GENE EDITING VARIATIONS IN NUCLEIC ACIDS

(71) Applicant: PIONEER HI-BRED INTERNATIONAL, INC., Johnston, IA (US)

(72) Inventors: Mary Beatty, Earlham, IA (US); Nicholas Doane Chilcoat, Clive, IA (US); Stephane Deschamps, West Des Moines, IA (US); Gregory D May, Ankeny, IA (US); Gina Marie Zastrow-Hayes, Urbandale, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 333 days.

(21) Appl. No.: 16/494,822

(22) PCT Filed: Mar. 29, 2018

(86) PCT No.: PCT/US2018/025033
§ 371 (c)(1),
(2) Date: Sep. 17, 2019

(87) PCT Pub. No.: WO2018/183607
PCT Pub. Date: Oct. 4, 2018

(65) Prior Publication Data
US 2020/0040378 A1 Feb. 6, 2020

Related U.S. Application Data

(60) Provisional application No. 62/478,660, filed on Mar. 30, 2017, provisional application No. 62/511,732, filed on May 26, 2017.

(51) Int. Cl.
*C12Q 1/6806* (2018.01)

(52) U.S. Cl.
CPC ..... *C12Q 1/6806* (2013.01); *C12Q 2521/301* (2013.01); *C12Q 2525/191* (2013.01); *C12Q 2531/113* (2013.01); *C12Q 2535/122* (2013.01); *C12Q 2563/179* (2013.01)

(58) Field of Classification Search
CPC ............ C12Q 1/6806; C12Q 2521/301; C12Q 2525/191; C12Q 2531/113; C12Q 2535/122; C12Q 2563/179
See application file for complete search history.

(56) References Cited

U.S. PATENT DOCUMENTS

| 10,329,574 B2 | 6/2019 | DuPont | |
| 10,519,457 B2 * | 12/2019 | Li | C12N 15/8216 |
| 2017/0073747 A1 * | 3/2017 | Joung | C12N 15/1093 |
| 2017/0321270 A1 * | 11/2017 | Haque | C12Q 1/6806 |

FOREIGN PATENT DOCUMENTS

| WO | 2015026886 | 2/2015 |
| WO | 20160186946 | 11/2016 |
| WO | 2019023590 A1 | 1/2019 |

OTHER PUBLICATIONS

Chen, Sean et al: "Highly Efficient Mouse Genome Editing by CRISPR Ribonucleoprotein Electroporation of Zygotes", Journal of Biological Chemistry, Jul. 8, 2016 (Jul. 8, 2016), vol. 291, No. 28, pp. 14457-14467.
Gabriel, Richard et al: "An Unbiased Genome-Wide Analysis of Zinc-Finger Nuclease Specificity", Nature Biotechnology, Jan. 1, 2011 (Jan. 11, 2011), vol. 29, No. 9, pp. 816-823.
Guilinger, John P et al: "Broad Specificity Profiling of Talens Results In Engineered Nucleases With Improved DNA-Cleavage Specificity", Nature Methods, Feb. 16, 2014 (Feb. 16, 2014), vol. 11, No. 4, pp. 429-435.
Kuscu, Cem et al: "Genome-Wide analysis reveals characteristics of off-target sites bound by the Cas9 endonuclease", Nature Biotechnology May 18, 2014, vol. 32 No 7, pp. 677-683.
Lee, Ciaran et al: "Nuclease target site selection for maximizing on-target activity and minimizing off-target effects in genome editing", Molecular Therapy: The Journal of the American Society of Gene Therapy, Mar. 1, 2016, vol. 24 No. 3, pp. 475-487.
Mandal, Pankaj K et al: "Efficient Ablation of Genes in Human Hematopoietic Stem and Effector Cells Using CRISPR/Cas9", Cell Stem Cell, Nov. 6, 2014 (Nov. 6, 2014), vol. 15, No. 5, pp. 643-652.
Pattanayak, Vikram et al: "High-throughput Profiling of Off-target DNA Cleavage Reveals RNA-programmed Cas9 Nuclease Specificity", Nature Biotechnology, Aug. 11, 2013 (Aug. 11, 2013), vol. 31, No. 9, pp. 839-843.
The International Search Report and Written Opinion for PCT/US2018/025033 (dated Sep. 12, 2018).
Akhras, Michael S.; et al.: "Connector Inversion Probe Technology: A Powerful One-Primer Multiplex DNA Amplification System for Numerous Scientific Applications", Plos One. vol. 2, No. 9, Jan. 1, 2007 (Jan. 1, 2007), pp. e915-e915.
Hardenbol, Paul; et al.: "Highly multiplexed molecular inversion probe genotyping: over 10,000 targeted SNPs genotyped in a single tube assay", Genome Research, Cold Spring Harbor Laboratory Press, US, vol. 15, No. 2, Feb. 1, 2005 (Feb. 1, 2005), pp. 269-275.
Wang, Guangchuan; et al.: "Pooled AAV-CRISPR Screen with Targeted Amplicon Sequencing", bioRxiv Jun. 22, 2017 (Jun. 22, 2017), pp. 1-51.

* cited by examiner

*Primary Examiner* — David C Thomas

(57) ABSTRACT

Compositions and methods of identifying and characterizing potential gene editing on-target and off-target sites and/or edits in a nucleic acid are provided.

27 Claims, No Drawings

METHODS OF IDENTIFYING AND CHARACTERIZING GENE EDITING VARIATIONS IN NUCLEIC ACIDS

CROSS-REFERENCE TO RELATED APPLICATIONS

This application is a 371 National Stage Entry of PCT/US18/25033, which claims priority to U.S. provisional patent application Ser. No. 62/478,660 filed Mar. 30, 2017, and Ser. No. 62/511,732 filed May 26, 2017, all of which are herein incorporated by reference in their entireties.

FIELD OF THE DISCLOSURE

The present disclosure relates to the field of genome editing and molecular biology.

BACKGROUND OF THE DISCLOSURE

Genome editing technologies, such as meganucleases, zinc finger nucleases, transcription activator-like effector nucleases (TALENS), CRISPR Cas endonucleases (such as but not limited to Cas9), other RNA-guided endonucleases, as well as base editing technology, have made it possible to edit the genome of many organisms, including plants and animals. While these technologies allow for targeted modification of sequences of interest, there is the potential for off-target genetic modification. There remains a need for methods and compositions to determine on-target and off-target gene editing sites and to measure off-target activity.

SUMMARY

Methods and compositions are provided for identifying and characterizing variations in a polynucleotide, for example variations due to edits created by a double-strand-break-inducing agent, a base-editing composition, by transformation with a heterologous polynucleotide, or by mutagenesis.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising generating nucleic acid fragments of the captured polynucleotide and recovering said fragments to create an enriched DNA pool.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising generating nucleic acid fragments of the captured polynucleotide and recovering said fragments to create an enriched DNA pool; further comprising characterizing the sequence composition of the enriched DNA pool to determine the nature of the enriched pool.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising generating nucleic acid fragments of the captured polynucleotide and recovering said fragments to create an enriched DNA pool; further comprising characterizing the sequence composition of the enriched DNA pool to determine the nature of the enriched pool; wherein the nature of the enriched pool comprises the composition and abundance of each sequenced fragment species.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is selected from the group consisting of: insertion of at least one nucleotide, deletion of at least one nucleotide, chemical modification of at least one nucleotide, substitution of at least one nucleotide, or a combination of any of the preceding.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a double-strand-break-inducing agent or a base editing molecule.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a double-strand-break-inducing agent or a base editing molecule; wherein said base editing molecule is a deaminase.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a double-strand-break-inducing agent or a base editing molecule; wherein said deaminase is a cytidine deaminase or an adenine deaminase.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a double-strand-break-inducing agent or a base editing molecule; wherein said double-strand-break-inducing agent is a Cas endonuclease, a meganuclease, a zinc finger nuclease, a transcription activator-like effector nuclease, or a restriction enzyme.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with a plurality of guide polynucleotides, to create a plurality of Cas9-guide polynucleotide complexes, wherein each guide polynucleotide directs the dCas9 protein to a different target site.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with a plurality of guide polynucleotides, to create a plurality of Cas9-guide polynucleotide complexes, wherein each guide polynucleotide directs the dCas9 protein to a different target site; wherein the plurality of guide polynucleotides comprises guides that are specific for the target site of the nucleic acid, non-specific for the target site of the nucleic acid, specific for one or more off-target sites, or combinations thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide, wherein the guide polynucleotide is selected for its potential to create off-target site edits.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide, wherein the guide polynucleotide is selected for the ability of the guide polynucleotide-Cas endonuclease complex to recognize and bind a sequence at or near the intended target site on the polynucleotide.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide, further comprising allowing the guide polynucleotide/Cas endonuclease complex to bind to the polynucleotide.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecule that binds to said polynucleotide but lacks substantial nuclease activity.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecule that binds to said polynucleotide but lacks substantial nuclease activity, wherein said molecule is a deactivated Cas9 (dCas9).

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecule that binds to said polynucleotide but lacks substantial nuclease activity, wherein the molecule further comprises a tag for protein purification or isolation.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a dCas9 that is linked to a tag for purification or isolation.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecule that binds to said polynucleotide but lacks substantial nuclease activity, wherein the molecule further comprises a tag for protein purification or isolation, wherein said tag is selected from the group consisting of: His tag, FLAG tag, HA tag, chitin binding protein (CBP) tag, maltose binding protein (MBP) tag, glutathione-S-transferase (GST) tag, thioredoxin (TRX) tag, poly(NANP) tag, V5-tag, Myc-tag, and NE-tag.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecule that binds to said polynucleotide but lacks substantial nuclease activity, wherein said molecule is a deactivated Cas9 (dCas9), wherein the dCas9 is complexed with a guide polynucleotide corresponding to a target sequence of interest on the polynucleotide.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide, further comprising eluting the guide polynucleotide-dCas9 protein-polynucleotide complex created in the capture step.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide, further comprising comparing the sequence of the target polynucleotide to a reference nucleic acid sequence to determine whether the guide polynucleotide directed the dCas9 to bind an intended target site on the polynucleotide of (a), a potential off-target site, or combination thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide; further comprising determining the ability of the guide polynucleotide/

Cas endonuclease complex to recognize and bind the intended target site on the nucleic acid.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein said at least one edit is created by a Cas endonuclease, wherein said Cas endonuclease is complexed with at least one guide polynucleotide; further comprising determining the guide polynucleotide/Cas endonuclease complex's preference for a sequence motif, the complex's binding strength to a particular sequence motif, or combinations thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein the molecular inversion probe comprises target arms that flank a target site on the nucleic acid.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein each molecular inversion probe comprises target arms that flank a different target site, off-target site, or a combination thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library; wherein the library comprises molecular inversion probes that are specific for the target site of the nucleic acid, non-specific for the target site of the nucleic acid, and/or combinations thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library; further comprising: hybridizing the polynucleotide with the molecular inversion probes from the molecular inversion probe library, recircularizing the hybridized molecular inversion probe using polymerase and ligase, subjecting the nucleic acid and molecular inversion probes to an exonuclease so that linear genomic DNA and un-circularized molecular inversion probes are digested, indexing and amplifying targeted sequences in a polymerase chain reaction (PCR) to produce indexed amplicons, and pooling and purifying the indexed amplicons.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library; further comprising: hybridizing the polynucleotide with the molecular inversion probes from the molecular inversion probe library, recircularizing the hybridized molecular inversion probe using polymerase and ligase, subjecting the nucleic acid and molecular inversion probes to an exonuclease so that linear genomic DNA and un-circularized molecular inversion probes are digested, indexing and amplifying targeted sequences in a polymerase chain reaction (PCR) to produce indexed amplicons, and pooling and purifying the indexed amplicons; wherein the indexing and amplifying targeted sequences use an indexed primer and non-indexed primer in the PCR to produce indexed amplicons.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library; further comprising: hybridizing the polynucleotide with the molecular inversion probes from the molecular inversion probe library, recircularizing the hybridized molecular inversion probe using polymerase and ligase, subjecting the nucleic acid and molecular inversion probes to an exonuclease so that linear genomic DNA and un-circularized molecular inversion probes are digested, indexing and amplifying targeted sequences in a polymerase chain reaction (PCR) to produce indexed amplicons, and pooling and purifying the indexed amplicons; wherein the indexing and amplifying targeted sequences use an indexed primer and non-indexed primer in the PCR to produce indexed amplicons; further comprising sequencing the pooled and purified indexed amplicons to generate sequence reads.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library; further comprising: hybridizing the polynucleotide with the molecular inversion probes from the molecular inversion probe library, recircularizing the hybridized molecular inversion probe using polymerase and ligase, subjecting the nucleic acid and molecular inversion probes to an exonuclease so that linear genomic DNA and un-circularized molecular inversion probes are digested, indexing and amplifying targeted sequences in a polymerase chain reaction (PCR) to produce indexed amplicons, and pooling and purifying the indexed amplicons; wherein the indexing and amplifying targeted sequences use an indexed primer and non-indexed primer in the PCR to produce indexed amplicons; further comprising sequencing the pooled and purified indexed amplicons to generate sequence reads; further comprising deconvoluting the sequence reads into sample bins by index sequence.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide is captured by a molecular inversion probe; wherein a plurality of molecular inversion probes are used to capture one or more variations of the polynucleotide, wherein the plurality of molecular inversion probes are pooled to generate a molecular inversion probe assay library; further comprising: hybridizing the polynucleotide with the molecular inversion probes from the molecular inversion probe library, recircularizing the hybridized molecular inversion probe using polymerase and ligase, subjecting the nucleic acid and molecular inversion probes to an exonuclease so that linear genomic DNA and un-circularized molecular inversion probes are digested, indexing and amplifying targeted sequences in a polymerase chain reaction (PCR) to produce indexed amplicons, and pooling and purifying the indexed amplicons; wherein the indexing and amplifying targeted sequences use an indexed primer and non-indexed primer in the PCR to produce indexed amplicons; further comprising sequencing the pooled and purified indexed amplicons to generate sequence reads; further comprising deconvoluting the sequence reads into sample bins by index sequence; further comprising analyzing the deconvoluted sequence by identifying reads that belong to a specific sample using the target arm of the MIP that flanks the 5' end of the target site, the target arm of the MIP that flanks the 3' end of the target site, or combinations thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the capturing of the polynucleotide is by a biotinylated probe.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the capturing of the polynucleotide is by a biotinylated probe; further comprising shearing of the polynucleotide prior to the capture step.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising comparing at least one sequence of (e) to a reference nucleic acid sequence.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising comparing at least one sequence of the assessing step to a reference nucleic acid sequence, comprising aligning said at least one sequence of (e) with the reference nucleic acid sequence and identifying at least one difference between said sequence and the reference nucleic acid sequence.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising comparing at least one sequence of the assessing step to a reference nucleic acid sequence, wherein the reference sequence does not comprise said target site edit, said off-target site edit, or combinations thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising cutting the captured polynucleotide into smaller fragments using random shearing or restriction digestion to generate a target site library of fragments.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is in an in vitro environment.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is from an oligonucleotide target site library.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is from a randomer nucleotide combinatorial target site library.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is in an in vivo environment.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is from a eukaryote or prokaryote.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is from a plant, mammal, insect, virus, fungus, or microorganism.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is from a plant selected from the group consisting of: maize, rice, sorghum, rye, barley, wheat, millet, oats, sugarcane, turfgrass, switchgrass, soybean, canola, alfalfa, sunflower, cotton, tobacco, peanut, potato, tobacco, *Arabidopsis*, vegetable, and safflower.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is genomic.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is synthetic.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein the polynucleotide that comprises the intended target site, an off-target site, or a combination thereof is isolated from its natural environment.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising determining the presence or absence of any off-target site edits, intended target site edits, or combinations thereof in the nucleic acid sequence.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein any two or more of the preceding steps are conducted essentially in parallel.

In one aspect, a method is provided for identifying or characterizing a plurality of variations in an edited polynucleotide, comprising: capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; wherein any two or more of the preceding steps are conducted essentially in parallel.

In one aspect, a method is provided for identifying or characterizing variations in a plurality of polynucleotides, comprising: capturing the polynucleotides that comprises at least one intended target site, off-target site, or a combination thereof, amplifying the captured polynucleotides to create a pool of polynucleotides, sequencing the pool, and assessing the pool of polynucleotides to identify sequences corresponding to the intended target site, sequences corresponding to an off-target site, or a combination thereof; wherein any two or more of the preceding steps are conducted essentially in parallel.

In any of the methods provided herein, a further step of editing a sequence of the polynucleotide based on the assessment of the presence or absence of the intended target site edit, off-target site edit, or combination thereof is provided.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof, optionally under various conditions or in different environments.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising evaluating the genotype or phenotype of the cell or organism at more than one time point.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising evaluating the genotype or phenotype of the organism in more than one cell type or tissue.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting at least one cell or individual of said organism that comprises said intended target site.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting at least one cell or individual of said organism that does not comprise at least one off-target site.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting at least one cell or individual of said organism that comprises said intended target site, does not comprise at least one off-target site, or comprises at least one off-target site; and further comprising growing said cell or organism.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting at least one cell or individual of said organism that comprises said intended target site, does not comprise at least one off-target site, or comprises at least one off-target site; and further comprising reproducing said cell or organism.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting at least one cell or individual of said organism that comprises said intended target site, does not comprise at least one off-target site, or comprises at least one off-target site; and further comprising crossing said organism with another to obtain a progeny, and evaluating said progeny for the presence or absence of the target and/or off-target sites.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting and reproducing or crossing at least one cell or individual of said organism that comprises said intended target site, does not comprise at least one off-target site, or comprises at least one off-target site; and further comprising selecting a progeny based on the determination of the presence or absence of the determined off-target site edit, the intended target site edit, or combinations thereof.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting and reproducing or crossing at least one cell or individual of said organism that comprises said intended target site, does not comprise at least one off-target site, or comprises at least one off-target site; and further comprising selecting a progeny that comprises the intended target site edit in its genome.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism comprising the intended target site edit, off-target site edit, or combinations thereof; further comprising selecting and reproducing or crossing at least one cell or individual of said organism that comprises said intended target site, does not comprise at least one off-target site, or comprises at least one off-target site; and further comprising selecting a progeny that does not comprise at least one off-target site edit in its genome.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising: evaluating the genotype or phenotype of a cell or an organism or a progeny thereof comprising the intended target site edit, off-target site edit, or combinations thereof; further comprising additional editing of the polynucleotide based on the assessment of the presence or absence of the intended target site edit, off-target site edit, or combination thereof in said cell, organism, or progeny.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising evaluating the genotype or phenotype of a cell or an organism or a progeny thereof comprising the intended target site edit, off-target site edit, or combinations thereof; wherein said cell, organism, or progeny is or is derived from a plant, mammal, virus, insect, fungus, or microorganism.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising evaluating the genotype or phenotype of a cell or an organism or a progeny thereof comprising the intended target site edit, off-target site edit, or combinations thereof; wherein said cell, organism, or progeny is or is derived from a plant selected from the group consisting of: maize, rice, sorghum, rye, barley, wheat, millet, oats, sugarcane, turfgrass, switchgrass, soybean, canola, alfalfa, sunflower, cotton, tobacco, peanut, potato, tobacco, *Arabidopsis*, vegetable, and safflower.

In one aspect, a method is provided for identifying or characterizing one or more variations in an edited polynucleotide, comprising: creating at least one edit in a polynucleotide at an intended target site, capturing the polynucleotide that comprises the intended target site, an off-target site, or a combination thereof, amplifying the captured polynucleotide to create a pool of polynucleotides, sequencing the pool, and assessing the pool of polynucleotides to identify sequences corresponding to the intended target site, sequences corresponding to an off-target site, or a combination thereof; further comprising identifying at least one potential gene editing off-target site using in silico techniques.

In one aspect, a method is provided for identifying a potential off-target site nucleotide variation, comprising: creating a polynucleotide variation at an intended target site, capturing said polynucleotide that comprises at least the intended target site, amplifying the captured polynucleotide(s) to create a pool of polynucleotides, sequencing the pool of polynucleotides, and assessing the pool of polynucleotides to identify sequences corresponding to the intended target site, sequences corresponding to an off-target site, or a combination thereof.

In one aspect, a method is provided for identifying a potential off-target site nucleotide variation, comprising: creating a polynucleotide variation at an intended target site, capturing said polynucleotide that comprises at least the intended target site, amplifying the captured polynucleotide(s) to create a pool of polynucleotides, sequencing the pool of polynucleotides, and assessing the pool of polynucleotides to identify sequences corresponding to the intended target site, sequences corresponding to an off-target site, or a combination thereof; further comprising identifying at least one off-target site.

In one aspect, a method is provided for identifying a potential off-target site nucleotide variation, comprising: creating a polynucleotide variation at an intended target site, capturing said polynucleotide that comprises at least the intended target site, amplifying the captured polynucleotide(s) to create a pool of polynucleotides, sequencing the pool of polynucleotides, and assessing the pool of polynucleotides to identify sequences corresponding to the intended target site, sequences corresponding to an off-target site, or a combination thereof; further comprising editing an off-target site.

In one aspect, a method is provided for identifying a potential off-target site nucleotide variation, comprising: creating a polynucleotide variation at an intended target site, capturing said polynucleotide that comprises at least the intended target site, amplifying the captured polynucleotide(s) to create a pool of polynucleotides, sequencing the pool of polynucleotides, and assessing the pool of polynucleotides to identify sequences corresponding to the intended target site, sequences corresponding to an off-target site, or a combination thereof; further comprising identifying at least one on-target site.

In one aspect, a method is provided for identifying a potential off-target site nucleotide variation, comprising: creating a polynucleotide variation at an intended target site, capturing said polynucleotide that comprises at least the intended target site, amplifying the captured polynucleotide(s) to create a pool of polynucleotides, sequencing the pool of polynucleotides, and assessing the pool of polynucleotides to identify sequences corresponding to the intended target site, sequences corresponding to an off-target site, or a combination thereof; further comprising editing at least one on-target site.

In one aspect, a method is provided for generating a portfolio of intended target sites, potential off-target sites or combinations thereof within a genome of interest, comprising: creating at least one nucleotide variation at an intended target site in a polynucleotide, capturing said polynucleotide that comprises at least one intended target site, an off-target site, or a combination thereof, amplifying the captured polynucleotide to create a pool of polynucleotides, sequencing the pool, identifying from the pool of polynucleotides to sequences corresponding to the intended target site, sequences corresponding to an off-target site, or a combination thereof, and selecting at least one sequence from the pool to include in the portfolio.

In one aspect, a method is provided for generating a portfolio of intended target sites, potential off-target sites or combinations thereof within a genome of interest, comprising: creating at least one nucleotide variation at an intended target site in a polynucleotide, capturing said polynucleotide that comprises at least one intended target site, an off-target site, or a combination thereof, amplifying the captured polynucleotide to create a pool of polynucleotides, sequencing the pool, identifying from the pool of polynucleotides to sequences corresponding to the intended target site, sequences corresponding to an off-target site, or a combination thereof, and selecting at least one sequence from the pool to include in the portfolio, wherein said sequence is represented in silico.

In one aspect, a method is provided for generating a portfolio of intended target sites, potential off-target sites or combinations thereof within a genome of interest, comprising: creating at least one nucleotide variation at an intended target site in a polynucleotide, capturing said polynucleotide that comprises at least one intended target site, an off-target site, or a combination thereof, amplifying the captured polynucleotide to create a pool of polynucleotides, sequencing the pool, identifying from the pool of polynucleotides to sequences corresponding to the intended target site, sequences corresponding to an off-target site, or a combination thereof, and selecting at least one sequence from the pool to include in the portfolio, wherein said sequence is a polynucleotide molecule placed in a biologically compatible environment in vitro.

In one aspect, a method is provided for generating a portfolio of intended target sites, potential off-target sites or combinations thereof within a genome of interest, comprising: creating at least one nucleotide variation at an intended target site in a polynucleotide, capturing said polynucleotide that comprises at least one intended target site, an off-target site, or a combination thereof, amplifying the captured polynucleotide to create a pool of polynucleotides, sequencing the pool, identifying from the pool of polynucleotides to sequences corresponding to the intended target site, sequences corresponding to an off-target site, or a combination thereof, and selecting at least one sequence from the pool to include in the portfolio, wherein said sequence is stored as a polynucleotide in a cell.

In one aspect, a method is provided for generating a portfolio of intended target sites, potential off-target sites or combinations thereof within a genome of interest, comprising: creating at least one nucleotide variation at an intended target site in a polynucleotide, capturing said polynucleotide that comprises at least one intended target site, an off-target site, or a combination thereof, amplifying the captured polynucleotide to create a pool of polynucleotides, sequencing the pool, identifying from the pool of polynucleotides to sequences corresponding to the intended target site, sequences corresponding to an off-target site, or a combination thereof, and selecting a plurality of sequences from the pool to include in the portfolio.

In one aspect, a nucleic acid target portfolio comprising a library of intended target sites and/or potential off-target sites generated from any of the methods described herein is provided.

DETAILED DESCRIPTION

The disclosure relates to compositions and methods of identifying and characterizing potential gene editing on-target and off-target sites in a nucleic acid. Identification of potential on-target and off-target site edits will allow for the selection of a guide polynucleotide and/or endonuclease that minimizes the risk of off-target site edits and increases the likelihood of intended on-target site edit(s). The presence or absence of on-target site edits and/or off-target site edits in a nucleic acid may be confirmed and, if desired, monitored in edited organisms using the methods and compositions described herein.

Definitions

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, a transgenic locus, or any other DNA molecule in the genome (including chromosomal, choroloplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeably herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but may be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example:
(i) replacement of at least one nucleotide, (ii) a deletion of at least one nucleotide,
(iii) an insertion of at least one nucleotide, (iv) substitution of at least one nucleotide,
(v) chemical modification of at least one nucleotide, or (vi) any combination of (i)-(v).

"Off-target site" means one or more alterations to a site other than the intended on-target site edit on a nucleic acid.

"On-target site" means one or more alterations to the intended site on a nucleic acid.

"Variation(s)", in the context of gene editing, refers to the range of polynucleotide modifications that are created by a particular agent (double-strand-break-inducing agent, or a base-editing composition. Such variations may comprise on-target edits, off-target edits, or a combination thereof.

"Cas9" (formerly referred to as Cas5, Csn1, or Csx12) herein refers to a Cas endonuclease that when in complex with a suitable polynucleotide component (such as crNucleotide and a tracrNucleotide, or a single guide polynucleotide) is capable of recognizing, binding to, and optionally nicking or cleaving all or part of a DNA target sequence. A Cas9 protein comprises a RuvC nuclease domain and an HNH (H-N-H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al., 2013, Cell 157:1262-1278). Cas9 endonucleases are sometimes derived from a type II CRISPR system, which includes a DNA cleavage system utilizing a Cas9 endonuclease in complex with at least one polynucleotide component (Makarova et al. 2015, Nature Reviews Microbiology Vol. 13:1-15).

The term "Cas endonuclease" herein refers to a protein encoded by a Cas (CRISPR-associated) gene. A Cas endonuclease, when in complex with a suitable polynucleotide component, is capable of recognizing, binding to, and optionally nicking or cleaving all or part of a specific DNA target sequence. Examples of Cas endonuclease include a Cas9 protein, a Cpf1 protein, a C2c1 protein, a C2c2 protein, a C2c3 protein, Cas3, Cas3-HD, Cas 5, Cas7, Cas8, Cas10, or complexes of these (Makarova et al. 2015, Nature Reviews Microbiology Vol. 13:1-15).

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide. "Open reading frame" is abbreviated ORF.

As used herein, the term "guide polynucleotide" relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence (referred to as guide RNA, gRNA), a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (See also U.S. Patent Application US 2015-0082478 A1, published on Mar. 19, 2015 and US 2015-0059010 A1, published on Feb. 26, 2015, both are hereby incorporated in its entirety by reference).

The term "genome" as it applies to a plant cells encompasses not only chromosomal DNA found within the nucleus, but organelle DNA found within subcellular components, for example, mitochondria, or plastid, of the cell.

The term "mammal" includes but is not limited to a pig, a horse, a rabbit, a goat, a cow, a cat, a dog, or a human.

Certain embodiments provide methods and compositions to identify potential gene editing off-target sites in DNA created by a site-specific nuclease, including, for example, ZFNs, TALENs, homing endonucleases, and any guided endonuclease, such as Cas endonuclease, e.g. CAS9/CRISPR. Such Cas endonucleases include, but are not limited to Cas9 and Cpf1 endonucleases. Other Cas endonucleases and nucleotide-protein complexes that find use in the methods disclosed herein include those described in WO 2013/088446. Any suitable method or technique may be used to identify the guide polynucleotide/Cas endonuclease for its potential to create on-target site edits or off-target site edits, including in vivo or in vitro assays. Alternatively or in addition, bioinformatics algorithms and in silico models or techniques can also be used to identify potential candidate off-target sites in DNA of interest.

In addition to the double-strand break inducing agents, site-specific base conversions can also be achieved to engineer one or more nucleotide changes to create one or more EMEs described herein into the genome. These include for example, a site-specific base edit mediated by an C·G to T·A or an A·T to G·C base editing deaminase enzymes (Gaudelli et al., Programmable base editing of A·T to G·C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C-→T (or G-→A on the opposite strand) or an adenine base editor that would convert adenine to inosine, resulting in an A-→G change within an editing window specified by the gRNA.

The target site may be located in a region outside of a gene sequence or within a gene sequence, for example, a regulatory sequence, a non-coding sequence or a coding sequence.

In certain embodiments, genes of interest for targeting include but are not limited to, for example, those genes involved in information, such as zinc fingers, those involved in communication, such as kinases, and those involved in housekeeping, such as heat shock proteins. More specific categories of transgenes, for example, include genes for encoding important traits for agronomics, insect resistance, disease resistance, herbicide resistance, fertility or sterility, grain characteristics, and commercial products. Genes of interest in certain embodiments include, generally, those involved in oil, starch, carbohydrate, or nutrient metabolism as well as those affecting kernel size, sucrose loading, and the like that can be stacked or used in combination with other traits, such as but not limited to herbicide resistance, described herein. In some embodiments, genes of interest include herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, fatty acids, and oil content and/or composition. In some embodiments, certain genes of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. Agronomically important traits such as oil, starch, and protein content can be genetically altered in addition to using traditional breeding methods. Modifications include increasing content of oleic acid, saturated and unsaturated oils, increasing levels of lysine and sulfur, introducing essential amino acids, and also modification of starch.

In certain embodiments, genes of interest for targeting include but are not limited to, for example, those genes involved in or associated with various diseases, such as cancer, memory-impacted diseases, hyperplasia, or cardiomyopathy. In certain embodiments, genes of interest for targeting include those involved in genetic diseases, such as cataract, Duchenne muscular dystrophy, hereditary tyrosinemia, cystic fibrosis, β-Thalassemia, or Urea cycle disorder. Genes targeted may include but are not limited to cystic fibrosis transmembrane conductor regulator (CFTR), crystallin gamma C (Crygc), dystrophin (Dmd), fumarylacetoacetate hydrolase (FAH), hemoglobin beta (HBB), or ornithine transcarbamylase (OTC). In certain embodiments, genes of interest for targeting include those involved in infectious diseases, including but not limited to human immunodeficiency virus (HIV), hepatitis B virus (HBV), Epstein-Barr virus (EBV), or human papillomavirus (HPV). Genes targeted for infectious disease may include but are not limited to HIV-1 LTR (long terminal repeat), HBV covalently closed circular DNA (cccDNA), Latent EBV in Burkitt's lymphoma cell line, or HPV oncogenes E6 and E7 in cancer cell lines.

In some embodiments, combinations of a particular Cas endonuclease and guide polynucleotide designs can be tested for their ability to recognize and bind on-target sites and off-target sites in a nucleic acid, for example, genomic DNA. In certain embodiments, a guide polynucleotide/Cas endonuclease complex that can bind, but not cleave, a target DNA sequence may be used to identify potential targets in genomic DNA. Such a complex may comprise a Cas protein in which all of its nuclease domains are mutant, dysfunctional. For example, a Cas9 protein that can bind to a DNA target site sequence, but not able to cleave one or more strands at the target site sequence, may comprise a mutant, dysfunctional RuvC domain, a mutant, dysfunctional HNH (H-N-H) nuclease domain. For example, the Cas endonuclease can comprise a modified form of the Cas9 polypeptide. The modified form of the Cas9 polypeptide can include an amino acid change (e.g., deletion, insertion, or substitution) that reduces the naturally-occurring nuclease activity of the Cas9 protein. See, for example, US patent application US20140068797 A1, published on Mar. 6, 2014. In some cases, the modified form of the Cas9 polypeptide has no substantial nuclease activity and is referred to as catalytically "inactivated Cas9" or "deactivated cas9 (dCas9)." Catalytically inactivated Cas9 variants include Cas9 variants that contain mutations in the HNH and RuvC nuclease domains. These catalytically inactivated Cas9 variants are capable of interacting with sgRNA and binding to the target site in vivo but cannot cleave either strand of the target DNA. See, US patent application US20140068797 A1, published on Mar. 6, 2014, a catalytically inactive Cas9 can be fused to a heterologous sequence.

The nucleic acid having potential target sites may be whole or in fragments, including but not limited to genomic DNA fragments. The nucleic acid may be isolated or synthetic in origin, such as synthesized oligonucleotides. The oligonucleotides or fragments having potential target sites may optionally be pooled into a library. As used herein, the term "target site library" means a library of nucleic acids comprising potential target sites. In some embodiments, the oligonucleotides or fragments may be used to make the target site library, which may be used for identifying which potential target sites on genomic DNA a guide polynucleotide/Cas endonuclease complex is capable of binding to. The nucleic acid in the library may be human, non-human, animal, bacterial, fungal, insect, yeast, non-conventional yeast, and/or plant DNA.

The step of screening for the ability of a particular guide polynucleotide/Cas endonuclease complex to bind potential off-target and on-target sites may include using a target site library. Use of the target site library in the methods and compositions herein provide for the simultaneous identification of a plurality of potential off-target sites and on-target edit sites for any particular guide polynucleotide/Cas endonuclease.

Incubation of different guide polynucleotide/Cas endonuclease complexes with the nucleic acid, for example, DNA, will result in binding of target sites in the target site library. Suitable conditions for subjecting the nucleic acid to the guide polynucleotide/Cas endonuclease complexes will be apparent to those of skill in the art.

The methods may also include identifying the sites on the nucleic acid that the particular guide polynucleotide/Cas endonuclease complex binds to, for example, binding of target sites. The binding sites may be off-target sites or on-target sites.

These binding sites may be identified using any suitable method that detects interactions between protein-nucleic acids including, e.g., ELISA, co-immunoprecipitation, bimolecular fluorescence complementation, affinity electrophoresis, pull-down assays, and the like. In some embodiments, the method is carried out using a tagged endonuclease. As exemplified herein, the endonuclease may be tagged to facilitate detection and immobilization of bound nucleic acids with target sites. Such tags include, e.g., a His-tag, FLAG-tag, V5-tag, HA-tag, c-myc-tag, chitin binding protein (CBP) tag, maltose binding protein (MBP) tag, glutathione-S-transferase (GST) tag, thioredoxin (TRX) tag, poly(NANP) tag, or NE-tag or combinations thereof, such as 1XFLAG-6XHis. In particular embodiments, the target molecule is biotinylated. For example, as described herein in Example 1, a His-tagged dCas9/gRNA or HA-epitope dCas9/gRNA is contacted with the target site library comprising potential target sites, and target nucleic acids/His-tagged dCas9/gRNA or HA-epitope dCas9/gRNA complexes are captured using HIS-coated beads or immunoprecipated using a HA antibody. Any unbound nucleic acids may be removed by washing.

Nucleic acids bound to the binding agents of interest may be isolated by any suitable technique, including but not limited to denaturation and recovery. Typically, these techniques involve dissociating the bound guide polynucleotide/Cas endonuclease complex from the target DNA. The target site on the DNA may be amplified using PCR, identified using molecular inversion probes (MIPs), identified using Southern by Sequencing technology and/or sequenced. With regard to Southern by Sequencing technology, see U.S. patent application Ser. No. 14/255,144; herein incorporated by reference in its entirety and as described elsewhere herein. The target site may be further characterized for composition, nature and abundance.

Any number of techniques and methodologies may be used to characterize the target sites. For example, the recovered nucleic acids may be hybridized with a probe, or primer that hybridizes to a region comprising the intended on-target site edit or off-target site edit, or using a primer pair to amplify a region comprising the intended on-target site edit or off-target site edit.

In another embodiment, the sequence is determined by sequencing. For example, linear amplification products may be analyzed directly without further amplification in some embodiments, for example, by using single-molecule sequencing methodology. Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion, for example, greater than $10^5$ molecules are sequenced simultaneously. In one embodiment, the relative abundance of the nucleic acid that was bound by the guide polynucleotide/Cas endonuclease can be estimated by counting the relative number of occurrences of their cognate sequences in the data generated by sequencing. Next generation sequencing instruments and methods are known in the art, and are described, e.g., in Metzker, M. (2010) Nature Biotechnology Reviews 11:31-46, incorporated herein by reference. See also for example next-generation sequencing platforms including, but not limited to, Oxford Nanopore Technologies, Illumina and Pacific Biosciences systems.

The sequence motif preference or binding strength to a particular sequence for a guide polynucleotide/Cas endonuclease complex may be determined from the data obtained. For example, preferential binding efficiencies may be calculated based on the ratio of sequencing reads corresponding to each binding motif. In turn, this information may be used to determine guide polynucleotide specificity and provide a target portfolio of potential on-target and off-target sites within a nucleic acid of interest for any particular guide polynucleotide. The methods and compositions provided herein allow those of skill in the art to design, identify, and/or select guide polynucleotides for generating specific desired on-target-site edits and/or decrease the likelihood for generating off-target site edits in DNA.

Once the particular guide polynucleotide and Cas endonuclease for making the intended on-target site edit are selected, the intended gene edit may be generated. In certain embodiments, the gene edit is a deletion, substitution, or insertion of a particular DNA sequence introduced at the target site or at a region near or adjacent to the target site. For example, the intended on-target site edit may be the specific introduction of a knock-out, edit, or knock-in at a particular DNA sequence, such as in a chromosome or plasmid of a cell. In some embodiments, genome editing may be performed herein by cleaving one or both strands at a specific DNA sequence in a cell with a Cas protein associated with a suitable polynucleotide component. Such DNA cleavage, if a double-strand break (DSB), may prompt NHEJ or HDR processes which may lead to modifications at the target site. The terms "knock-in", "gene knock-in", "gene insertion" and "genetic knock-in" are used interchangeably herein. A knock-in represents the replacement or insertion of a DNA sequence at a specific DNA sequence in a cell by genome editing using a guide polynucleotide and Cas endonuclease in combination with donor DNA polynucleotide. Examples of knock-ins are a specific insertion of a heterologous amino acid coding sequence in a coding region of a gene, or a specific insertion of a transcriptional regulatory element in a genetic locus. Various methods and compositions may be employed to obtain a cell having a polynucleotide of interest inserted in a target site for a Cas endonuclease. Such methods may employ homologous recombination to provide integration of the polynucleotide of interest at the target site. In one method provided, a polynucleotide of interest is provided to the organism cell in a donor DNA construct.

As used herein, "donor DNA" includes reference to a DNA construct that comprises a polynucleotide of interest to be inserted into the target site of a Cas endonuclease. In some embodiments, the donor polynucleotide may correct a mutant gene and/or increase expression of an endogenous gene, for example, by inserting a sequence not present in the target site of interest. The donor polynucleotide may be a natural or a modified polynucleotide. The donor DNA construct may further comprise a first and a second region of homology that flank the polynucleotide of Interest. The first and second regions of homology of the donor DNA share homology to a first and a second genomic region, respectively, present in or flanking the target site of the cell or organism genome. The donor DNA may be tethered to the guide polynucleotide and/or the Cas endonuclease. Tethered donor DNAs may allow for co-localizing target and donor DNA, useful in genome editing and targeted genome regulation, and may also be useful in targeting post-mitotic cells where function of endogenous HR machinery is expected to be highly diminished (Mali et al. 2013 Nature Methods Vol. 10: 957-963.) The donor polynucleotide may be either single-stranded or double-stranded.

Furthermore, it is recognized that the polynucleotide of interest may also comprise antisense sequences complementary to at least a portion of the messenger RNA (mRNA) for a targeted gene sequence of interest. In addition, the polynucleotide of interest may also be used in the sense orientation to suppress the expression of endogenous genes in the organism. Methods for suppressing gene expression in the organism using polynucleotides in the sense orientation are known in the art. The methods generally involve introducing into the cell or organism a DNA construct comprising a promoter that drives expression in the organism or specific cell-type or tissue operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, U.S. application 62/023,246, filed on Jul. 7, 2014, and U.S. application 62/036,652, filed on Aug. 13, 2014, all of which are incorporated by reference herein.

For example, a guide polynucleotide/Cas endonuclease system may be used to modify or replace nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest. See, for example, U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein.

Generally, the methods of introducing a guide polynucleotide/Cas endonuclease complex into a cell include methods of introducing at least one guide polynucleotide and at least one Cas endonuclease protein into a cell, and growing said cell under suitable conditions to allow said guide polynucleotide and said Cas endonuclease protein to form a complex inside said cell. In embodiments where a polynucleotide of interest is to be inserted into the target site, donor DNA may be introduced by any means known in the art. In certain embodiments, the intended on-target site edit may be made with the guide polynucleotide-Cas endonuclease and optionally donor polynucleotide depending on the type of desired edit (insertion edit) in cells inside the organism (in vivo), in cells outside of the organism but delivered back to the organism (ex vivo), or in cells outside of the organism (in vitro).

Accordingly, a polynucleotide of interest may be provided and integrated into the organism's genome at the target site and expressed in the organism. The organism may be further evaluated for a particular phenotype, function or expression level.

Nucleic acids and proteins may be provided to a cell by any method including methods using molecules to facilitate the uptake of anyone or all components of a guided Cas system (protein and/or nucleic acids), such as cell-penetrating peptides and nanocariers. See also US20110035836 Nanocarier based plant transfection and transduction, and EP 2821486 A1 Method of introducing nucleic acid into plant cells, incorporated herein by reference.

The methods of the present disclosure allow for the identification of DNA edited by the particular guide polynucleotide/Cas endonuclease complex. In certain embodiments, the method includes confirming the presence of the intended on-target site edit and/or absence of the off-target site edit in the target sequence of the nucleic acid in a cell of the organism. The methods may include selecting from a group of plants, mammals, viruses, insects, fungi, or microorganisms, one or more plants, mammals, viruses, insects, fungi, or microorganisms that comprise the intended target site edit in its nucleic acid. The intended on-target edit or off-target site edit may include a deletion, insertion of a donor polynucleotide, or substitution or combinations thereof, for example, in a target site in genomic DNA.

In certain embodiments, the method of confirming the presence or absence of the intended on-target site edit or off-target site edit includes but is not limited to use of a PCR based method or assay, Southern blot assay, Northern blot assay, protein expression assay, Western blot assay, ELISA assay, MIP technology, or Next Generation Sequencing and any combination thereof. See, for example, U.S. patent application Ser. No. 12/147,834, and U.S. patent application Ser. No. 14/255,144, The Plant Genome. (March 2015) 8:1 (1-15), the content of each of which is incorporated by reference herein in its entirety. These methods may include the use of a primer or probe of the target sequence, intended on-target edit sequence or off-target site edit sequence. For example, in some embodiments, the methods may include the use of a primer or probe that hybridizes to a region comprising the intended on-target site edit or off-target site edit or the use of a primer pair to amplify a region comprising the intended on-target site edit or off-target site edit.

In certain embodiments, the methods and compositions described herein use molecular inversion probes (MIP) technology to detect or amplify particular nucleic acid sequences. Use of MIP technology allows for the detection of changes at the single nucleotide level without prior knowledge of the exact edit that is generated at each site. The MIPs technology may be used to characterize both the region of desired editing as well as potential off target locations in the genome that may also exhibit editing with specific guide species. Accordingly, in certain embodiments, the methods and compositions described herein include but are not limited to the use of MIP assays in determining target site sequences, for example, intended on-target site edits or off-target site edits. In certain embodiments, the MIPs have targeting arms that flank DNA regions of interest. As used here, "targeting arms" means sequences that have homology to the desired nucleic acid region surrounding the target site. The DNA regions of interest may include the intended on-target sites and potential off-target sites or combinations thereof. The targeting arms may be designed to hybridize upstream and downstream of one or more specific on-target site edit sequence or potential off-target site edit sequence located on DNA. In some embodiments, the targeting arm may include a sequence that is complementary to the intended on-target site or off-target site. The targeting arm may be designed to hybridize to one or the other strand of DNA.

The MIPs are allowed to hybridize to nucleic acid to perform capture of target sequences located on the template. Incubation of one or more different MIPs with the DNA will allow the targeting arms to hybridize upstream and downstream of one or more specific on-target site edit sequences or potential off-target site edit sequences on the DNA. Suitable conditions for hybridizing MIPs to DNA will be apparent to those of skill in the art. The hybridized MIPs may be recircularized using polymerase and ligase enzymes to fill and seal the gap between the two probe ends, two arms, forming a covalently-closed circular molecule that contains the target sequence. The recircularized MIPs may be subjected to an exonuclease digestion to degrade linear genomic DNA and un-circularized probes. See, for example, U.S. Pat. Nos. 5,866,337; 7,790,388; 6,858,412; 7,993,880; 7,700,323; 6,558,928; 6,235,472; 7,320,860; 7,351,528; 7,074,564; 5,871,921; 7,510,829; 7,862,999; and 7,883,849, the content of each of which is incorporated by reference herein in its entirety. The circular target probes may optionally be pooled into a panel, which may be used for characterizing one or more on-target site sequences or potential off-target site edit sequences on a nucleic acid, for example, DNA. The advantages of this approach include the ability to pool and assay many sites in parallel.

The captured target sequences of interest may be indexed and amplified and the resulting indexed amplicons may be pooled and purified. See, for example, Beckman Ampure XP (Danvers, Mass.). In some embodiments, adaptors for sequencing may be attached during PCR or to linear post-capture amplicons. In some embodiments, each adaptor may contain a unique identifier for each probe, for example, barcodes, such that the unique identifier does not appear within the probe or targeted sequence.

Purified amplicon pools may be sequenced using any suitable approach as described herein and known to one skilled in the art. In certain embodiments, sequencing reads may be deconvoluted into sample bins by index sequence. The per sample reads may be analyzed using identifying reads that belong to a specific MIPs assay via the 5' and 3' targeting arm. The aligned reads or targeted MIPs sequence may be compared to a suitable control or reference sequence that does not have the intended on-target site edit or wildtype reference sequence, for example, one that was used to design the original assays. Differences between the reference sequences may be identified by comparison of nucleotides at certain positions or looking for mismatches in sequence alignment.

In certain embodiments, the methods and compositions described herein use Southern by Sequencing (SbS) technology to detect both the region of desired editing as well as potential off target locations in the genome that may also exhibit editing with specific guide species. Constructs used in the transformation of the gene editing constructs may also be detected using the methods, such as SbS, and compositions described herein. Use of SbS technology allows for the detection of changes at the single nucleotide level.

In certain embodiments, the methods and compositions described herein include but are not limited to the use of SbS approaches in determining or monitoring edited target site sequences, for example, intended on-target site edit sequences or off-target site edit sequences.

In certain embodiments, SbS employs a sequence capture-based method that enriches sequencing libraries, such as Illumina™ or PACBIO™ sequencing libraries, for nucleic acid fragments comprising fragments of constructs used in the process of making the intended gene edit, intended on-target site edit sequences, or potential off-target site edit sequences, or combinations thereof.

Next generation DNA shotgun libraries for individual gene-edited events may be used in the methods described herein. See, for example, Example 5. The nucleic acid in the library may be human, non-human, animal, bacterial, fungal, insect, yeast, non-conventional yeast, and/or plant DNA. Nucleic acid, such as genomic DNA, may be isolated or extracted from various materials, for example, edited genetic materials of all species including, human, non-human, animal, bacterial, fungal, insect, yeast, non-conventional yeast, and/or plant DNA, using any number of techniques known to one skilled in the art and/or as described elsewhere herein. In one example, genomic DNA may be isolated from plant, for example, from leaf punches. In some examples, the DNA is purified and assessed for quality and quantity. The DNA of the individual gene-edited event may be fragmented into smaller DNA fragments using restriction enzymes or sonication. The ends of the DNA may be end-repaired if desired. Adapter sequences may be ligated to the ends of the fragments, for example, via blunt or sticky-end ligations depending on the technique utilized to fragment the DNA and whether the DNA fragment ends were end-repaired. In some embodiments, each adaptor may contain a unique identifier for each probe, for example, barcode, such that the unique DNA identifier does not appear elsewhere within the probe or targeted sequence. As used herein, a "barcode" be also be referred to as a "tag", "multiplex identifier", or "index" sequence and may link a sequence or read to its library or source (pool). In some examples, the barcode may be flanked by a specific sequence that is used for attaching the fragment to the flow cell, such as a Illumina™ specific sequence. In some embodiments, the adaptors may be flanked by one or more barcodes to enable sample pooling at the hybridization and/or sequencing stages. In some embodiments, each sample has a barcode. The captured target sequences of interest may be indexed and amplified and the resulting indexed amplicons may be pooled and purified. See, for example, Beckman Ampure XP (Danvers, Mass.). In some embodiments, adaptors for sequencing may be attached during PCR or to linear post-capture amplicons.

Ligated fragment libraries may be amplified. See, for example, NimbleGen™ capture protocols, SeqCap EZ Library: Technical Note "Double Capture: High Efficiency Sequence Capture of Small Targets." (2012). Together, the DNA fragments with attached barcodes form fragment libraries that can be enriched via PCR amplification using any suitable primers, for example, adapter-specific PCR primers. The ligated fragment libraries may be pooled, for example, in equal molar ratios.

A probe library that contains probes for various intended on-target site edits, potential off-target site edits, or DNA constructs used in the process of making the intended on-target edit, or combinations thereof may be created. The probes may have homology to a nucleic acid region surrounding the intended on-target site or potential off-target site, or have homology to a nucleic acid region that includes the intended on-target site, potential off-target site, or combinations thereof. Additionally, the probes may have homology to a DNA construct used in the process of making the intended on-target edit. The probes may be designed to hybridize upstream and downstream of one or more specific intended on-target site edit sequence or potential off-target site edit sequence located on DNA. In some embodiments, the probe may include a sequence that is complementary to the intended on-target site sequence or off-target site sequence. The probe may be designed to hybridize to one or the other strand of DNA.

In a further embodiment, the method utilizes a labeled probe library comprising sequence fragments containing constructs used the process of making the intended edit, sequences of intended on-target site edits, sequences of potential off-target site edits or combinations thereof. Any suitable label may be used to label the probe, including but not limited to biotinylation.

Sequence fragments containing intended target site edits or potential off-target site edits of interest may be analyzed as a collection and reduced to a set of unique sequences representing all bases within the collection. The DNA probe library is designed such that nearly all bases within a construct pool, regions containing one or more intended on-target site edits, region containing one or more potential off-target site edits, or combinations thereof are targeted during the enrichment process. The construct pool includes any construct used in the genome editing process, including but not limited to transformation and guideRNA constructs. The probe library may be in solution, glass slide, or plate microarray or any other suitable environment.

The probes are allowed to hybridize to the nucleic acid to perform capture of target sequences located in the fragment and/or event. Incubation of one or more different probes with the DNA will allow the probes to hybridize upstream and downstream of one or more specific intended on-target site edit sequences, potential off-target site edit sequences, or combinations thereof on the DNA. In some examples, incubation of one or more different probes with the DNA will allow the probes to hybridize to the constructs used in the process of making the intended on-target edits. Suitable conditions for hybridizing probes to DNA will be apparent to those of skill in the art. The probes may optionally be pooled into a library, which may be used for characterizing one or more intended on-target site edit sequences or potential off-target site edit sequences on a nucleic acid, for example, DNA. The advantages of this approach include the ability to pool and assay many target sites in parallel, including intended on-target site edits and potential off-target site edits.

Sequence enrichment or capture may be accomplished using any number of methods as described elsewhere herein and known to one skilled in the art. In some embodiments, a double capture approach may be used to increase on target reads. See, for example, NimbleGen™ protocols. In one embodiment, DNA libraries comprising the individual events or fragments may be denatured and incubated with a labeled probe library, such as a biotinylated probe library. DNA fragments in the libraries that bind to one or more probes in the library may be isolated using any suitable technique, for example, using beads, columns or other solid support capable of binding to the label on the probe, including but not limited to Streptavidin Dynabeads. In some examples, the library pools may be washed and eluted.

Washed and eluted library pools may optionally be amplified and/or captured. In some examples, the library pools may be amplified and purified a second time using methods known to one skilled in the art and as described elsewhere herein.

Final capture library pools may be quantified and diluted for sequencing. Purified amplicon pools may be sequenced using any suitable approach as described herein and known to one skilled in the art. In certain embodiments, sequencing reads may be deconvoluted into sample bins by index sequence. The per sample reads may be analyzed using identifying reads that belong to a specific barcode.

The reads can be aligned to the sequence of a control or reference sequence, for example, a corresponding genomic sequence that does not contain the intended on-target gene edit. In some embodiments, reads that align to the control or reference sequence and are identical in sequence, are considered "endogenous reads". Endogenous reads may be excluded from further analysis in the methods disclosed herein. In certain embodiments, the reads for an event or sample may be first compared to a reference sequence of a construct that was used in the process of making the intended on-target site edit. Junction sequences between the plasm id/construct and the genomic segment may be identified using the processes described in U.S. patent application Ser. No. 14/255,144; herein incorporated by reference in its entirety.

If the read for an event does not align to the construct reference sequence, the read may be aligned to a reference sequence that comprises potential off-target site edit sequences. If no potential off-target sites are determined or identified for the event or sample, then the reads may be aligned to a reference sequence that comprises the intended on-target site edit sequence to identify, confirm or monitor the intended on-target edit. See, for example, Example 6, described herein. The comparisons of the reads to the various reference sequences may be performed in any order desired. Methods of alignment of sequences for comparison are well known in the art. Computer implementations of these mathematical algorithms can be utilized for comparison of sequences to determine optimum alignment, for example, CLUSTAL; the ALIGN program, GAP, BESTFIT, BLAST, FASTA, and TFASTA in the GCG and the like. Alignments using these programs can be performed using the default parameters.

Differences between the reference sequences may be identified by comparison of nucleotides at certain positions or looking for mismatches in sequence alignment. Generated sequence may be used to identify fragments of any construct used in the genome editing process, any intended on-target site edit sequence, any off-target site edit sequence, or combinations thereof, and the integrity of the intended on-target site and off-target site.

In certain embodiments, the presence or absence of the intended on-target site edit(s) and/or absence of the off-target site edit(s) may be detected based on the expression of the targeted gene, for example, a change in the expression level or temporal or spatial expression pattern of the targeted gene, for example, when compared to the expression level, temporal or spatial expression pattern of a control or reference gene that does not have the same intended on-target site edit(s). In some examples, the methods described herein include growing the organism, such as a plant or animal, that has the confirmed intended on-target site edit and/or absence of off-target site edits for further testing and evaluation.

In some instances, the method includes using the selected organism, such as the plant or animal, that that has the confirmed intended on-target site edit and/or absence of off-target site edits for use in a breeding program. For example, when the organism is a plant, the plant having the intended on-target site edit and/or absence of off-target site edits may be used in recurrent selection, bulk selection, mass selection, backcrossing, pedigree breeding, open pollination breeding, restriction fragment length polymorphism enhanced selection, genetic marker enhanced selection, double haploids and transformation. In some instances the plant may be crossed with another plant or back-crossed so that the intended on-target site edit may be introgressed into the plant by sexual outcrossing or other conventional breeding methods.

In some instances, the intended on-target site edit may be used as a marker for use in marker-assisted selection in a breeding program to produce plants or animals that have the phenotype of the plant or animal with the intended on-target site edit.

For example, the phenotype may include an alteration in the expression level of a protein of interest whose sequence is modified, inserted or deleted by the intended on-target edit, for examples, increasing or decreasing expression of the protein. Examples include but are not limited to increasing the copy number of coding sequence that encodes the protein of interest, modifying the endogenous coding sequence that encodes the protein of interest, or modifying the endogenous promoter or regulatory elements that are driving the endogenous coding sequence encoding the protein of interest, for example, inserting a heterologous element, until the desired level of protein is detected in the sample from the organism. In addition to or alternatively, when the level of protein of interest detected or quantified is present in low amounts, decisions may be made on protein presence, absence, or range specific expression; and the assays, methods, and systems may optionally include culling plants or animals that express the protein of interest in non-desired or sub-optimal amounts, or growing or breeding plants or animals which express the protein of interest in desired or optimal amounts. In certain embodiments, off-target cutting is observed prior to medical therapy that utilizes an active or inactive Cas9.

In certain embodiments, the presence or absence of the intended on-target site edit and/or off-target site edits are monitored in the progeny or subsequence generations of the organisms. Any suitable method or technique may be used to monitor the presence or absence of any intended on-target site edits and/or any off-target site edits. The presence or absence of the edits at the target sites on the DNA may be determined using any suitable method or technique described herein or known to one skilled in the art. Examples include but are not limited to PCR based methods or assays, Southern blot assays, Northern blot assays, protein expression assays, Western blot assays, ELISA assays, MIP technologies, or Next Generation Sequencing and any combination thereof. These methods may include the use of a primer or probe of the target sequence, intended on-target edit sequence or off-target site edit sequence or combinations thereof. For example, in some embodiments, the methods may include the use of a primer or probe that hybridizes to a region comprising the intended on-target site edit or off-target site edit or the use of a primer pair to amplify a region comprising the intended on-target site edit or off-target site edit.

The following examples are offered by way of illustration and not by way of limitation.

EXAMPLES

The embodiments are further defined in the following Examples, in which parts and percentages are by weight and degrees are Celsius, unless otherwise stated. It should be understood that these Examples, while indicating embodiments of the disclosure, are particular by way of illustration only. From the above discussion and these Examples, one skilled in the art can ascertain the essential characteristics of the embodiments, and without departing from the spirit and scope thereof, can make various changes and modifications of them to adapt to various usages and conditions. Thus, various modifications of the embodiments in addition to those shown and described herein will be apparent to those skilled in the art from the foregoing description. Such modifications are also intended to fall within the scope of the appended claims. The disclosure of each reference set forth herein is incorporated herein by reference in its entirety.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the appended claims.

Example 1

Use of dCas9 for Capture of Nucleic Acid

Use of the methods and compositions described herein allow for rapid and cost-effective identification and characterization of potential gene editing off target sites in the genomes of various species. This information can be used to determine and characterize the sequence specificity of gene editing tools (guide [targeting] nucleic acids, novel enzymes). In addition, this information can be used to monitor for unintended (off intended target) gene edit events in edited genetic materials of all species including, plants, microbes, virus and mammals. In one example, modified Cas9 protein, labeled as "dCas9", is tagged with 6XHis tags and FLAG epitope for subsequent extraction of the guide polynucleotide/Cas endonuclease-nucleic acid bound complex. The dCas9 protein still has the ability to bind DNA (when complexed with a guide polynucleotide target) but is unable to subsequently cut the DNA region it is bound. As a result, the binding of dCas9 is directed to bind to a synthetic oligonucleotide or specific genomic regions after random shearing or restriction digestion of the genome, for example, in a target site library, using guide polynucleotides corresponding to sequence of interest. After binding, the guide polynucleotide/Cas endonuclease complex bound to nucleic acid in this example can be eluted using His beads or immunoprecipitation with an anti-HA antibody. Recovery of the enriched DNA fragments can then be performed via a simple denaturation step (phenol/chloroform/ethanol, for example) or via PCR amplification directly off the bead/synthetic oligonucleotide complex, using PCR primers annealing directly to universal sequences located at the 5' and 3' ends of the bound oligonucleotides. Subsequently, sequence composition of the enriched DNA pool is characterized to determine the nature (composition and abundance of each sequenced fragment species) of the enriched pool. This information is used to determine the sequence specificity of the gene editing tools by determining the ability of these tools to recognize and bind target sequence. The sequence motif preference or binding strength to a particular sequence can be determined with the data obtained. In turn, this information can determine gene editing tool specificity and provide a target portfolio of potential target and off-target sites within a genome of interest for any particular guide polynucleotide. In the latter example, this information is used to monitor off-target gene modifications in gene edited biological materials, for example a cell. In some embodiments, the protocol would include the following steps: 1) generation of a dCas9-gRNA complex; 2) random shearing of genomic DNA to size of interest and generating a target site library (e.g., Illumina) of sheared fragments—OR—synthesizing a randomer nucleotide combinatorial target site library); 3) binding of dCas9-gRNA complex to sheared genomic DNA or target site library; 4) elution of bound DNA fragments with His beads or immunoprecipitation; 5) denaturation—OR—PCR amplification, and recovery of DNA fragment for further handling, including DNA sequencing.

This approach has several advantages including 1) the possibility of isolating multiple genomic regions in parallel including the intended target and potential off-site targets; 2) the possibility of isolating genomic regions of varying sequence composition, including sequence not known to exist in a reference genome; 3) isolation of genomic DNA regions from various lines and species of interest; 4) no requirement for extensive probe design and no need for extensive knowledge of the sequence for the same region in other lines and/or species; 5) low cost and protocols amenable to high-throughput isolation; and 6) the ability to use this approach in any line or species of interest with only a minimum knowledge of the sequence of the targeted region(s) or combinations thereof.

Methods

1) Preparation of Tagged dCas9

A tagged dCas9 was prepared using one of two ways.

In one experiment, a commercial tagged dCas9 was purchased directly from New England Biolabs (NEB—Catalog Number M0652S) and used directly for the enrichment assay. The commercial dCas9 is tagged with a SNAP-tag® which is a "highly engineered version of AGT (alkylguanine DNA alkyltransferase)". See New England Biolabs FAQ: What is the SNAP-tag®?

In a second experiment. a purified tagged dCas9 was expressed in $E.$ $coli$ from a vector containing a tagged dCas9 gene. In the latter experiment, an expression vector containing a tagged Cas9 (SP) (ALT1)-1XFLAG-6XHis gene is transformed into $E.$ $coli$ BL21. Two liters of 2X-YT media plus kanamycin are inoculated with 0.1% overnight culture and grown at 37° C. until OD600~0.7. The temperature is reduced to 16° C. and cultures are induced with 0.1 mM IPTG. Cultures are incubated at 16° C. overnight. Cells are harvested by centrifugation at 8,000 g for 20 min (JLA8.1 Rotor, 6,500 rpm). Pellets are stored at −20° C.

1 liter shake-flask pellet of CAS9 (SP) (ALT1)-1XFLAG-6XHis protein is re-suspended in 50 ml Buffer A (20 mM Tris, pH 8.0, 500 mM NaCl) with 2.5 U/ml Benzonase and Complete Protease Inhibitor and mixed at 4° C. for 10 minutes. The cells are lysed using homogenizer (two passes at 25 kpsi). The lysate is clarified by centrifugation for 20 min (SS-34 rotor, 16,000 RPM). The supernatant is collected. The supernatant is passed over one 2 ml His-Pur Superflow Ni-NTA column that is pre-equilibrated with 10CV of buffer A. The column is sequentially washed with 10CV buffer A, 10CV buffer B (20 mM Tris, pH 8.0, 500 mM NaCl, 1% Triton X-100) and 5CV buffer A. The protein is sequentially eluted from the column with 5CV buffer C (20 mM Tris, pH 8.0, 500 mM NaCl, 10% Glycerol)+10 mM imidazole, 5CV buffer C+20 mM imidazole, 5CV buffer C+50 mM imidazole and 2CV buffer C+250 mM imidazole (for E250, added buffer and mixed well and let the column sit for 10 minutes before collecting). The 4 ml E250 elution sample is diluted 1:10 to reduce the imidazole concentration to 25 mM and 20 ml is stored at 4° C. pending cation exchange chromatography. The 20 ml E250 elution sample is concentrated to 2 ml and diluted 1:10 in 20 mM Tris, pH 8.0, 10% glycerol to create 20 ml of protein sample in the following buffer condition prior to cation exchange chromatography: 20 mM Tris, pH 8.0, 50 mM NaCl, and 2.5 mM imidazole. The 20 ml protein sample (~8.5 mg) are loaded onto a 1 ml HiTrap S P FF cation exchange column pre-equilibrated with 20 mM Tris, pH 8.0, 10% glycerol, eluted over 20CV with a 0-100% 1M NaCl gradient in 20 mM Tris, pH 8.0, 10% glycerol and collected in 1 ml fractions. The protein concentration of the final pooled sample is measured by Bradford assay using BSA as standard. The sample is aliquoted into 19 vials of 0.2 ml each and stored at −20° C.

2) Preparation of Template DNA

Different types of template DNA can be used, including randomer nucleotide combinatorial target site library, genomic templates or large clone (BAC) templates.

In this particular example, a randomer nucleotide combinatorial target site library was used for the experiment. Prior to capture and enrichment, random 24-mer single-stranded oligonucleotides flanked by universal adapters (Integrated DNA Technologies, Coralville, Iowa) were made double-stranded by primer extension in a solution containing 0.88 µM template, 88 µM primer, 1×Taq-Pro Complete, 2.0 mM MgCl2 (Denville Scientific).

3) Capture and Enrichment of Targeted Genetic Sequences

Capture of targeted genetic sequences was performed using either the commercial tagged dCas9 from NEB or the purified tagged dCas9 expressed in, and purified from, $E.$ $coli.$ The purified dCas9 (64 nM) was mixed with 192 nM sgRNA (crRNA and tracrRNA) in 1×Cas9 nuclease reaction buffer (100 nM HEPES, pH 7.4; 750 mM KCl; 50 nM MgCl2; 25% glycerol)) in the presence of 3 µg template DNA, then incubated at 37 C for 4 hours. Several methods can be used for recovering bound DNA/dCas9/sgRNA complex, including immunoprecipitation with anti-FLAG antibody (monoclonal or polyclonal), bead-based pull-down or Ni-NTA agarose. The method described below will focus on the use of Dynabeads™ His-Tag magnetic beads (Thermo Fisher) for isolation and pull-down assay.

50 µl magnetic bead re-suspension of His-Tag beads (2 mg) (Thermo, Prod. #: 10103D) was used for the pull-down assay. The His-Tag beads were washed twice with 200 µl 1×Binding/Wash buffer (50 mM Sodium-Phosphate, pH 8.0; 300 mM NaCl; 0.01% Tween™-20). DNA/protein complex (prepared in 1×Binding/Wash buffer) in 100 µl total reaction volume was added to the His-Tag magnetic beads in a micro centrifuge tube and incubated for 10 min at room temperature with rotation. After incubation, the tube was placed on a magnet for 2 min, then the supernatant was discarded. The beads were washed 4 times with 0.3 ml 1×Binding/Wash buffer by placing the tube on the magnet for 2 min after resuspension and discarding the supernatant. To elute the protein, 100 µl of 1×His Elution buffer (300 nM Imidazole; 50 mM Sodium-Phosphate, pH 8.0; 300 mM NaCl; 0.01% Tween™-20) was added to the His-Tag beads. After incubation on a roller for 5 min at room temperature, the tube was placed on a magnet for 2 min and the supernatant containing the eluted histidine-tagged protein/DNA complex was transferred to a clean tube and used as template for PCR amplification.

The capture assay with the commercial tagged dCas9 was performed under the same conditions but in the presence of 1×NEB3.1 reaction buffer. The recovery of bound DNA/ dCas9/sgRNA complex was performed using commercial beads from NEB (SNAP-Capture Magnetic beads, Catalog number S9145S), following the manufacturer's recommendations and using 1×NEB3.1 buffer as immobilization buffer. The binding assay was incubated at 4° C. overnight, with mixing. After washing, the tag-bound DNA/dCas9/sgRNA complex was used as template for PCR amplification.

In both instances, recovery was performed by PCR amplification. After PCR and PCR clean-up, amplified oligonucleotides were sequenced on the Illumina platform.

4) Data Analysis

Alignment of the resulting sequencing data to their respective gRNA sequences suggested either modest enrichments (~2× to 6×increase, depending on the motif analyzed) for the experiment performed with the purified tagged dCas9, in comparison to the presence of said sequences in negative control samples (e.g., no gRNA in binding reaction), Alignments showed no specific enrichment for the experiment performed with the commercial tagged dCas9, Both experiments showed high level of non-specific oligonucleotide sequences in both the enriched and negative control samples.

Example 2

Molecular Inversion Probe for Targeting Gene Edited Nucleic Acids—Molecular Inversion Probe Design Molecular inversion probes assays were first designed by analyzing a 100 basepair window surrounding the target site of interest, for example a 100 basepair window. A target site of interest for CAS9 molecular characterization was defined as a desired edit site or a potential off target site identified through off-target assay or in-silico analysis of guide polynucleotide sequences across the genome. Targeting arms flanking the region of interest were selected based on the following assay criteria: arm length of 17-28 basepairs, distance between 5' and 3' targeting arms of 1-70 basepairs and predicted melting temperature of 68-72 degrees Celsius. Following design, targeting arms for each assay were linked by a common backbone sequence 30-50 basepairs in length and ordered as individual oligos with a 5' phosphorylation. The individual 250 uM MIPs oligos are pooled in equal volumes to generate a 250 uM assay pool.

MIPs Targeting and Amplification

MIPs targeting and sequencing pooling creation was accomplished via a four step process: hybridization, circularization, exonuclease digestion and indexing/amplification. Briefly, hybridization reactions were prepared by combining 250 ng of DNA with 1.25 ul ampligase buffer (Epicentre), 0.5 ul 1 M blocking oligo, a volume of MIPs assay pool that resulted in a DNA:MIPs ratio of 500:1 to 5000:1 depending on panel size, and water to a final reaction volume of 12.5 ul. Reactions were denatured for 10 minutes at 95 degrees Celsius followed by three hour incubation at 60 degrees Celsius in a thermocycler with heated lid. Following incubation hybridized MIPs were recirculated by addition of 0.2 ul of 10×Ampligase buffer, 1 ul 2 U/ul HF Phusion polymerase (New England Biolabs), 0.25 ul 100 U/ul Ampligase enzyme (Epicentre) and 0.55 ul 0.25 mM dNTP mix (New England Biolabs) to the completed hybridization reaction, while the reaction was maintained at 60 degrees Celsius. The final circularization reaction was mixed gently, sealed and incubated at 60 degrees Celsius for 16-18 hours. Following circularization, incubation reactions were collected by centrifugation, incubated for 1 minute at 37 degrees Celsius and stored at 4 degrees Celsius until exonuclease digestion.

Exonuclease digestion to remove linear genomic DNA and un-circularized probes were performed by adding 1 ul of 20 U/ul Exo I and 1 ul of 100 U/ul Exo III (New England Biolabs) to the circularized MIP reaction from the previous step. Reactions were incubated in a thermocycler for 15 minutes at 37 degrees Celsius followed by a 2 minute inactivation at 95 degrees Celsius. Following digestion, targeted sequences were indexed and amplified by adding 12.5 ul of 2×iProof Master mix (Biorad), 0.125 ul 100 uM universal backbone forward primer, 0.125 ul 100 uM indexed backbone reverse primer, and 9.8 ul water. Reactions were denatured at 98 degrees for 2 minutes and amplified by 25 cycles of 98 degrees for 10 seconds, 60 degrees for 30 seconds, 72 degrees for 60 seconds. Resulting indexed amplicons are pooled and purified by a 1:1 Ampure XP cleanup according manufacturers recommendations (Beckman). Purified amplicon pools were sequenced via Illumina recommendations on MiSeq sequencers, generating 100 basepair paired end reads. Sequencing reads were deconvoluted into sample bins by index sequence. Per sample reads were analyzed by identifying reads that belong to a specific MIPs assay via the 5' and 3' targeting arm. Reads were aligned via Bowtie version 2 to the wildtype reference that is used to design the original assays. Differences between the reference sequences were identified by mismatches in alignment and reported via SAM Tools.

Allele sequences for 121 loci comprising on and off target loci were targeted and successfully detected in 760 plants. Alleles at both on target and off-target loci were characterized mutations detected. Plants with mutations at both the desired on-target locus and additional off-target loci were characterized through subsequent generations via molecular inversion probes and confirmed the process can be used to characterize allele segregation.

Example 3

Example of Identifying and Characterizing Target Sites

Potential gene editing off-target sites can be identified to optimize selection of guide polynucleotide design in an effort to reduce the number of potential, unintentional off-target edits using the methods described in Example 1. Based on criteria and considerations including nucleotide sequence composition and uniqueness of the target site within the genome to be edited, a guide polynucleotide is selected and used for gene editing. Methods to determine guide polynucleotide potential off-target sites are described in Example 1. Example 1 teaches that combinations of nuclease/gRNA designs can be tested in vitro for their ability to recognize and bind target and off-target DNA oligonucleotides or fragments. In this method, candidate gRNAs and a modified, tagged CAS9 protein that has lost its ability to cut double stranded DNA (e.g., dCAS9) are incubated in a reaction containing a combinatorial pool of synthesized double-stranded oligonucleotides or randomly sheared genomic DNA fragments. The tagged dCAS9 protein/oligonucleotide complexes are enriched and DNA sequence analysis is performed to identify candidate off-target sites bound by the dCAS9/gRNA complex. Alternatively, bioinformatics algorithms can also be used to identify candidate off-target sites in genomes of interest. The product of Example 1 is a list and/or target site library of candidate target sites which can be used to determine the suitability of a particular gRNA design, or can be used to develop a MIPs panel to screen edited materials to survey for unintended gene edits at candidate off-target sites as described in Example 2. In this example, the panel is comprised of between 1 and 100,000 candidate target and off-target sites. This panel is determined from the results of Example 1 or 3 or from in silico prediction. In Example 1, inclusion of a sequence in the panel, based on the ranked likelihood that a specific sequence, or based on its relative abundance determined by sequence analysis (sequence counting), could be targeted by a particular nuclease/gRNA combination. In practice, gene editing can be carried out by any suitable method. To determine whether the intended target edit is created, the nucleic acid can be sequenced using conventional methods or targeted as described in Example 2. Sequence results obtained from genome editing are characterized candidate off-target sites in edited biological materials and enable the determination if unintended gene editing has occurred at these sites.

Example 4

Tiling Method

Using sequence information from the genomic on-target site and potential off-target site sequence, ligation mediated nested PCR (LMN-Tiling primers) are designed. Assay sensitivity and specificity is determined by the nested PCR primer design, in which two primers are designed for every 200 base pairs on alternating stands, or 400 base pair spacing on a single strand.

Following primer design, DNA is extracted from lyophilized leaf punches using the EZNA Plate 96™ kit (Omega Biotek, Norcross, Ga.). Purified genomic DNA is assessed for quality and quantity with a Fragment Analyzer™ (Advanced Analytical, Ames, Iowa) and subsequently sheared to an average fragment size of 1500 base pairs with a Covaris E210™ (Covaris Inc, Woburn, Mass.). Sheared DNA is end repaired, A-Tailed, and ligated according to the protocols provided by Kapa Biosystems™ (Woburn, Mass.). Ligated adapters are custom designed with ninety-six unique, six base-pair barcodes and linked to the Illumina P7™ sequence to enable Illumina sequencing post-PCR.

Following ligation, fragment libraries are enriched for intended on-target site or potential off-target site sequences by two rounds of twenty cycle amplification. Primary PCR utilizes the first primer of the nested pair as the forward primer and an adapter-specific primer as the reverse primer, anchoring one end of each amplicon. Secondary PCR paired the adapter-specific primer with the nested PCR primer, which includes the Illumina P5™ sequence, finishing the fragments for Illumina™ sequence. Following purification with AmpureXP™ beads (Beckman Genomics, Danvers, Mass.), fragment libraries are analyzed on the Fragment Analyzer™, pooled in equal molar ratios into ninety six sample pools and diluted to 2 nM. Pools are sequenced on the Illumina (San Diego, Calif.) MiSeq or HiSeq 2500™ system, generating one to two million 100 base pair paired end reads per sample as per manufacturer protocols.

Generated sequence is used to identify the on-target site sequence, off-target sequence and integrity of the on-target site and/or off-target site.

Example 5

Southern by Sequencing Approach

The Southern by Sequencing (SbS) application employs a sequence capture based method to enrich sequencing libraries for sequence fragments containing constructs used in the process of making one or more intended gene edits, intended on-target site sequences, potential off-target site sequences or combinations thereof, for example, using Illumina™ or PACBIO sequencing libraries (Zastrow-Hayes, G. M., H. Lin, A. L. Sigmund, J. L. Hoffman, C. M. Alarcon, K. R. Hayes, T. A. Richmond, J. A. Jeddeloh, G. D. May, and M. K. Beatty. 2015. Southern-by-Sequencing: A Robust Screening Approach for Molecular Characterization of Genetically Modified Crops. Plant Genome 8. doi:10.3835/plantgenome2014.08.0037). A biotinylated probe library is designed and synthesized. Sequence fragments containing intended on-target site edits or potential off-target site edits of interest are analyzed as a collection and reduced to a set of unique sequences representing all bases within the collection. A DNA probe library is designed such that nearly all bases within a construct pool, intended on-target site region and potential off-target site region are targeted during the enrichment process.

Following probe library design, next generation DNA shotgun libraries are produced for individual gene-edited events via standard molecular manipulations. With respect to a plant example, in brief, DNA is isolated from leaf punches via Omega Biotek (Norcross, Ga.) EZNA Plant 96™ kit. Purified genomic DNA is assessed for quality and quantity with a Fragment Analyzer™ (Advanced Analytical, Ames, Iowa) and subsequently sheared by sonication to an average fragment size of 400 bp with a Covaris E210™ (Covaris Inc, Woburn, Mass.). Sheared DNA is end repaired, A-Tailed, and ligated according to the protocols provided by Kapa Biosystems™ (Woburn, Mass.).

The ligated B100 Scientific (Austin, Tex.) NEXTFlex™ adapter sequences includes ninety six unique six base pair bar-codes flanked by Illumina™ specific sequences to enable sample pooling at the hybridization and sequencing stages.

To support efficient pooling of samples, index barcodes are incorporated into the Illumina library construction process by adding them into Illumina's I5™ adapter and utilizing the standard Illumina barcodes in Illumina's I7™ adapter. Pared with Illumina's I7 adapter barcodes, this provides the means to run over 2000 samples together with a unique barcode identifier on each sample.

Ligated fragment libraries are amplified eight cycles according NimbleGen™ capture protocols. Amplified libraries are once again assessed for quality and quantity with the Advanced Analytical Fragment Analyzer™, pooled in equal molar ratios in groups of 24, 48, or 96 and diluted to a working stock of 5 ng/ul.

Sequence enrichment is accomplished according to the NimbleGen™ protocols, utilizing a double capture approach to increase on-target reads. DNA shotgun libraries described above are denatured in a cocktail with hybridization buffers, SeqCap EZ Developer Reagent™, and blocking oligos corresponding to the adapter sequences in the pool. Post denaturation, the cocktail is combined with the biotinylated oligo library and incubated at forty-seven degrees Celsius for sixteen hours. Following the hybridization, the cocktail is mixed with streptavidin Dyanbeads M-270™ (LifeTech, Grand Island, N.Y.). Using the DynaMag-2™ (LifeTech, Grand Island, N.Y.) the bound DNA fragments are washed according to the NimbleGen™ capture protocol. Washed and eluted library pools are amplified five cycles, purified according to manufacturer instructions with Qiagen (Germantown, Md.) Qiaquick™ columns, and then captured, amplified sixteen cycles, and purified a second time using the methods described above.

Final capture library pools are quantified with the Agilent tape station and diluted to 2 nM for sequencing. Pools are sequenced on the Illumina™ (San Diego, Calif.) MiSeq™ or HiSeq 2500 System™, generating one to two million 100 base pair paired-end reads per sample.

Generated sequence is used to identify fragments of any construct used in the genome editing process, any intended on-target site edits, any potential off-target site edits, and the integrity of the on-target and/or off-target sites.

Example 6

Southern by Sequencing Bioinformatic Pipeline

SbS can be used to identify one or more intended on-target site edits, potential off-target site edits, integration site, copy number, integrity, backbone presence, and rearrangement of the plasmid insertions by detecting chimeric junction sequences between transformation plasmid and genomic DNA or noncontiguous plasmid DNA, or combinations thereof. The representative sequences may be aligned to the genome or reference sequence comprising the desired intended on-target site edit. The genome or reference sequence may be human, non-human, animal, bacterial, fungal, insect, yeast, non-conventional yeast, and/or plant.

In cases where the genome has been edited only, for example, the reads are screened for any construct or plasmid that is used in the gene editing process to ensure that none are inadvertently integrated into the gene edited event's genome. For example, junctions between the plasm id/construct and the genomic segment may be identified.

Reads that do not align to or contain plasm id/construct sequences may be further analyzed. For example, reads may be aligned to a genome reference sequence. Endogenous reads that align to the genome not containing the intended on-target site edit or off-target site edit are identified and excluded from further analysis. The remaining reads are aligned to a reference sequence comprising the intended on-target site edit or potential off-target site edit sequence and determined if the sequence has the intended on-target gene edit or potential off-target site edit.

If desired, the reads may be extended from the gene edited target site edit, such as the intended on-target edit site and/or off-target edit site, into longer contigs using clean reads. An advancement decision, for example, for a plant event, may be made based on a set of criteria based on the analysis result, the on-target site sequence, off-target sequence, integrity of the on-target site and off-target site, and fragments of any construct used in the process.

This pipeline works well for enriched sequences of the constructs used in the process of making the intended edit, intended on-target site or potential off-target site sequences and the flanking sequences generated by sequence capture method. It can also be applied for whole genome shotgun sequencing of the human, non-human, animal, bacterial, fungal, insect, yeast, non-conventional yeast, and/or plant genomes including transgenic and/or gene edited human, non-human, animal, bacterial, fungal, insect, yeast, non-conventional yeast, and/or plant cells.

Use of SbS is a high-throughput pipeline that minimizes the advancement of poor gene-edited events so that time and money is not spent further on poor gene-edited events, for example, with respect to plants, in the downstream product development stages of plant lines.

What is claimed is:

1. A method of identifying and characterizing variations of an edited polynucleotide, comprising:
    (a) creating at least one edit in a polynucleotide at an intended target site in a plant cell;
    (b) capturing by one or more molecular inversion probes the polynucleotide that comprises the intended target site, an off-target site, or a combination thereof, wherein the one or more molecular inversion probes comprise target arms that flank the intended target site or the off-target site on the nucleic acid;
    (c) amplifying the captured polynucleotide of (b) to create a pool of polynucleotides;
    (d) sequencing the pool of (c); and
    (e) assessing the pool of polynucleotides to identify sequences corresponding to the intended target site, sequences corresponding to an off-target site, or a combination thereof.

2. The method of claim 1, further comprising generating nucleic acid fragments of the captured polynucleotide and recovering said fragments to create an enriched DNA pool.

3. The method of claim 2, further comprising characterizing the sequence composition of the enriched DNA pool to determine the nature of the enriched pool.

4. The method of claim 3, wherein the nature of the enriched pool comprises the composition and abundance of each sequenced fragment species.

5. The method of claim 1, wherein the polynucleotide of (b) comprises one or more variations, wherein the one or more molecular inversion probes is a plurality of molecular inversion probes, and wherein the plurality of molecular inversion probes are used to capture the one or more variations of the polynucleotide of (b), wherein each molecular inversion probe comprises target arms that flank a different target site, off-target site, or a combination thereof.

6. The method of claim 5, wherein the plurality of molecular inversion probes are pooled to generate a molecular inversion probe assay library.

7. The method of claim 6, wherein the library comprises molecular inversion probes that are specific for the target site of the nucleic acid, non-specific for the target site of the nucleic acid, and/or combinations thereof.

8. The method of claim 6, the method further comprising:
    (f) hybridizing the polynucleotide with the molecular inversion probes from the molecular inversion probe library,
    (g) recircularizing the hybridized molecular inversion probe using polymerase and ligase,
    (h) subjecting the nucleic acid and molecular inversion probes to an exonuclease so that linear genomic DNA and un-circularized molecular inversion probes are digested,
    (i) indexing and amplifying targeted sequences in a polymerase chain reaction (PCR) to produce indexed amplicons, and
    (j) pooling and purifying the indexed amplicons, and
    (k) sequencing the pooled and purified indexed amplicons to generate sequence reads.

9. The method of claim 8, wherein the indexing and amplifying targeted sequences use an indexed primer and non-indexed primer in the PCR to produce indexed amplicons.

10. The method of claim 8, further comprising deconvoluting the sequence reads into sample bins by index sequence.

11. The method of claim 10, further comprising analyzing the deconvoluted sequence by identifying reads that belong to a specific sample using the target arm of the MIP that flanks the 5' end of the target site, the target arm of the MIP that flanks the 3' end of the target site, or combinations thereof.

12. The method of claim 1, further comprising comparing at least one sequence of (e) to a reference nucleic acid sequence.

13. The method of claim 12, comprising aligning said at least one sequence of (e) with the reference nucleic acid sequence and identifying at least one difference between said sequence and the reference nucleic acid sequence.

14. The method of claim 12, wherein the reference sequence does not comprise said target site edit, said off-target site edit, or combinations thereof.

15. The method of claim 1, further comprising cutting the captured polynucleotide of (b) into smaller fragments using random shearing or restriction digestion to generate a target site library of fragments.

16. The method of claim 1, wherein the polynucleotide of (a) is in an in vitro environment.

17. The method of claim 1, wherein the polynucleotide of (a) is from an oligonucleotide target site library.

18. The method of claim 17, wherein the target site library is a randomer nucleotide combinatorial target site library.

19. The method of claim 1, comprising performing steps (b), (c), and (d) in parallel so that multiple nucleic acids can be characterized.

20. The method of claim 1, further comprising additional editing of the polynucleotide based on the assessment of the presence or absence of the intended target site edit, off-target site edit, or combination thereof.

21. The method of claim 1, the method further comprising: evaluating the genotype or phenotype of a cell or an organism comprising the intended target site edit, off-target site edit, or combinations thereof, optionally under various conditions, at one or more time point(s), in one or more cell type(s) or tissue(s), or in different environments.

22. The method of claim 1, wherein said plant is selected from the group consisting of: maize, rice, sorghum, rye, barley, wheat, millet, oats, sugarcane, turfgrass, switchgrass, soybean, canola, alfalfa, sunflower, cotton, tobacco, peanut, potato, tobacco, *Arabidopsis*, vegetable, and safflower.

23. A method for generating a portfolio of intended target sites, potential off-target sites or combinations thereof within a genome of interest, comprising:
(a) creating at least one nucleotide variation at an intended target site in a polynucleotide;
(b) capturing by one or more molecular inversion probes the polynucleotide that comprises the intended target site, an off-target site, or a combination thereof, wherein the one or more molecular inversion probes comprise target arms that flank the intended target site or the off-target site on the nucleic acid;
(c) amplifying the captured polynucleotide of (b) to create a pool of polynucleotides;
(d) sequencing the pool of (c);
(e) identifying from the pool of polynucleotides to sequences corresponding to the intended target site, sequences corresponding to an off-target site, or a combination thereof; and
(f) selecting at least one sequence from (e) to include in the portfolio.

24. The method of claim 23, wherein the sequence of (f) is represented in silico.

25. The method of claim 23, wherein the sequence of (f) is a polynucleotide molecule placed in a biologically compatible environment in vitro.

26. The method of claim 23, wherein the sequence of (f) is stored as a polynucleotide in a cell.

27. The method of claim 23, comprising a plurality of sequences of (f).

* * * * *